(12) United States Patent
Wang

(10) Patent No.: US 11,925,330 B2
(45) Date of Patent: Mar. 12, 2024

(54) MOUTH MIRROR APPARATUS

(71) Applicant: Sheng-Peng Wang, Taipei (TW)

(72) Inventor: Sheng-Peng Wang, Taipei (TW)

( * ) Notice: Subject to any disclaimer, the term of this patent is extended or adjusted under 35 U.S.C. 154(b) by 514 days.

(21) Appl. No.: 17/176,910

(22) Filed: Feb. 16, 2021

(65) Prior Publication Data
US 2021/0393119 A1   Dec. 23, 2021

(30) Foreign Application Priority Data

Jun. 18, 2020   (TW) .................................. 109120534

(51) Int. Cl.
| | | |
|---|---|---|
| *A61B 1/253* | (2006.01) | |
| *A61B 1/00* | (2006.01) | |
| *A61B 1/12* | (2006.01) | |

(52) U.S. Cl.
CPC .......... *A61B 1/253* (2013.01); *A61B 1/00091* (2013.01); *A61B 1/128* (2013.01)

(58) Field of Classification Search
CPC ......... A61B 1/126; A61B 1/247; A61B 1/253; A61B 2018/2283; A61B 1/00091; A61B 1/128; A61C 17/088; A61C 3/00; A61C 3/088
USPC ......................................................... 433/30
See application file for complete search history.

(56) References Cited

U.S. PATENT DOCUMENTS

| | | | | |
|---|---|---|---|---|
| 3,859,987 A | * | 1/1975 | Holstad ................. | A61B 1/253 433/30 |
| 4,261,637 A | * | 4/1981 | King ..................... | A61B 1/253 433/30 |
| 4,279,594 A | * | 7/1981 | Rigutto ................. | A61B 1/253 433/95 |
| 6,575,744 B1 | * | 6/2003 | Oshida .................. | A61B 1/127 359/872 |
| 2016/0360957 A1 | * | 12/2016 | Wang .................... | A61B 1/253 |

FOREIGN PATENT DOCUMENTS

| | | | |
|---|---|---|---|
| EP | 0387216 A1 | * | 9/1990 |
| EP | 2181643 | * | 5/2010 |
| FR | 1301672 A | * | 9/1961 |
| KR | 20110043170 A | * | 4/2011 |

* cited by examiner

*Primary Examiner* — Edward Moran
*Assistant Examiner* — Matthew P Saunders
(74) *Attorney, Agent, or Firm* — Osha Bergman Watanabe & Burton LLP

(57) ABSTRACT

A mouth mirror apparatus includes a carrier seat that has first and second receiving spaces and multiple outlet passages embedded in a surrounding wall and intercommunicating the first and second receiving spaces. The mouth mirror apparatus further includes a handle grip cooperating with the carrier seat to define an air inlet passage that communicates with the second receiving space, a mirror body rotatably disposed in the first receiving space, and an impeller connected to the mirror body and driven by air which flows from the air inlet passage. Through combination of the mirror body, the impeller, and the arrangement of the air outlet passages, the mouth mirror apparatus can direct air current to render different functions.

13 Claims, 10 Drawing Sheets

MOUTH MIRROR APPARATUS

CROSS-REFERENCE TO RELATED APPLICATION

This application claims priority of Taiwanese Patent Application No. 109120534, filed on Jun. 18, 2020.

FIELD

The disclosure relates to a mouth mirror apparatus, and more particularly to a mouth mirror apparatus having a rotating mirror module.

BACKGROUND

During a dental procedure, water droplets splashed on the surface of a mouth mirror often blocks the reflection in the mouth mirror. In order to solve the problem, a conventional mouth mirror apparatus is provided with a rotating mirror driven by a motor, which prevents water droplets from attaching to the rotating mirror. However, since the motor is driven by electric power, such mouth mirror apparatus is susceptible to electrical leakage.

Another conventional mouth mirror apparatus uses pneumatic power to drive rotation of the rotating mirror. Such conventional mouth mirror apparatus has an air inlet opening that is located close to the rotating mirror, and is connected to a suction device that draws air via the air inlet opening to drive the rotation of the rotating mirror. Although such pneumatic mouth mirror apparatus is safer than its electric counterpart, the rotation of the rotating mirror is often slowed down when fluid (e.g., saliva of a patient) is drawn into the air inlet opening or the air inlet opening is blocked by debris. Besides, the air current will reduce the temperature of the rotating mirror and, as a result, the surface of the rotating mirror can become foggy when its temperature falls below the intra-oral temperature.

SUMMARY

Therefore, the object of the disclosure is to provide a mouth mirror apparatus that can alleviate at least one of the drawbacks of the prior art.

According to the disclosure, a mouth mirror apparatus includes a handheld module and a rotating mirror module.

The handheld module includes a carrier seat and a handle grip. The carrier seat has a surrounding wall, a mounting wall and a base cover.

The surrounding wall surrounds an axis. The mounting wall extends transversely to the axis, and is surrounded by and connected to the surrounding wall.

The surrounding wall and the mounting wall cooperatively define first and second receiving spaces that are disposed on two sides of the mounting wall that are opposite along the axis, and a plurality of air outlet passages that are embedded angularly at intervals in the surrounding wall. Each of the air outlet passages has a first passage open end communicating the first receiving space and a second passage open end communicating the second receiving space. The base cover covers an opening of the second receiving space, and is connected to the surrounding wall. The handle grip is transversely connected to an outer surface of the surrounding wall, and cooperates with the surrounding wall to define an air inlet passage in spatial communication with the second receiving space.

The rotating mirror module includes a mirror unit and an impeller.

The mirror unit has a mirror body disposed in the first receiving space transversely to the axis, and being rotatable about the axis relative to the carrier seat, and a rotary shaft extending through the mounting wall along the axis, and co-rotatably connected to the mirror body.

The impeller has a connecting hub disposed in the second receiving space, and co-rotatably connected to the rotary shaft, and a plurality of fan blades arranged angularly about the axis in the second receiving space, and co-rotatably connected to the connecting hub. The fan blades are adapted to be driven by air, which travels through the air inlet passage into the second receiving space, to drive the rotation of the mirror body of the mirror unit relative to the carrier seat.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
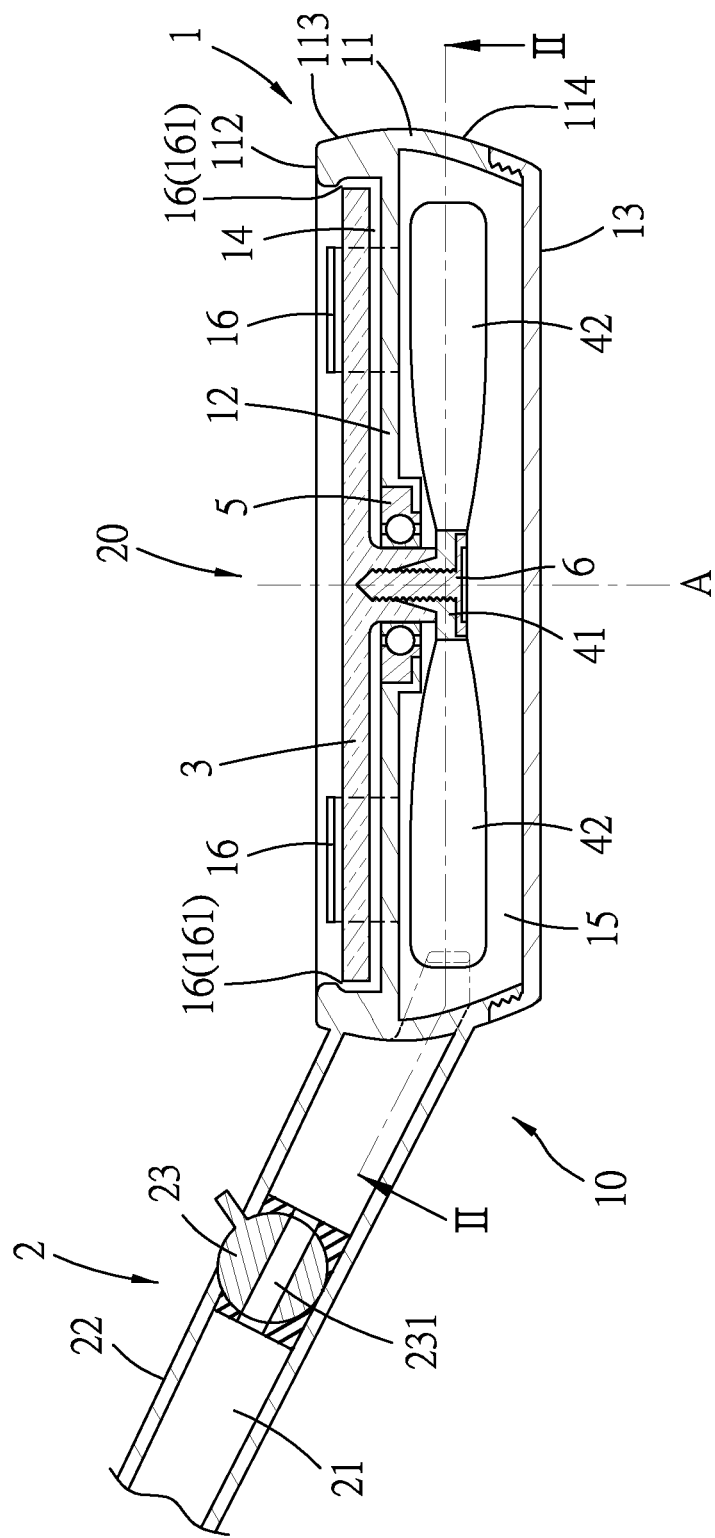
FIG. 1 is a fragmentary sectional view illustrating a first embodiment of a mouth mirror apparatus according to the disclosure.

Before the present disclosure is described in greater detail, it should be noted that where considered appropriate, reference numerals or terminal portions of reference numerals have been repeated among the figures to indicate corresponding or analogous elements, which may optionally have similar characteristics.

Figure 2:
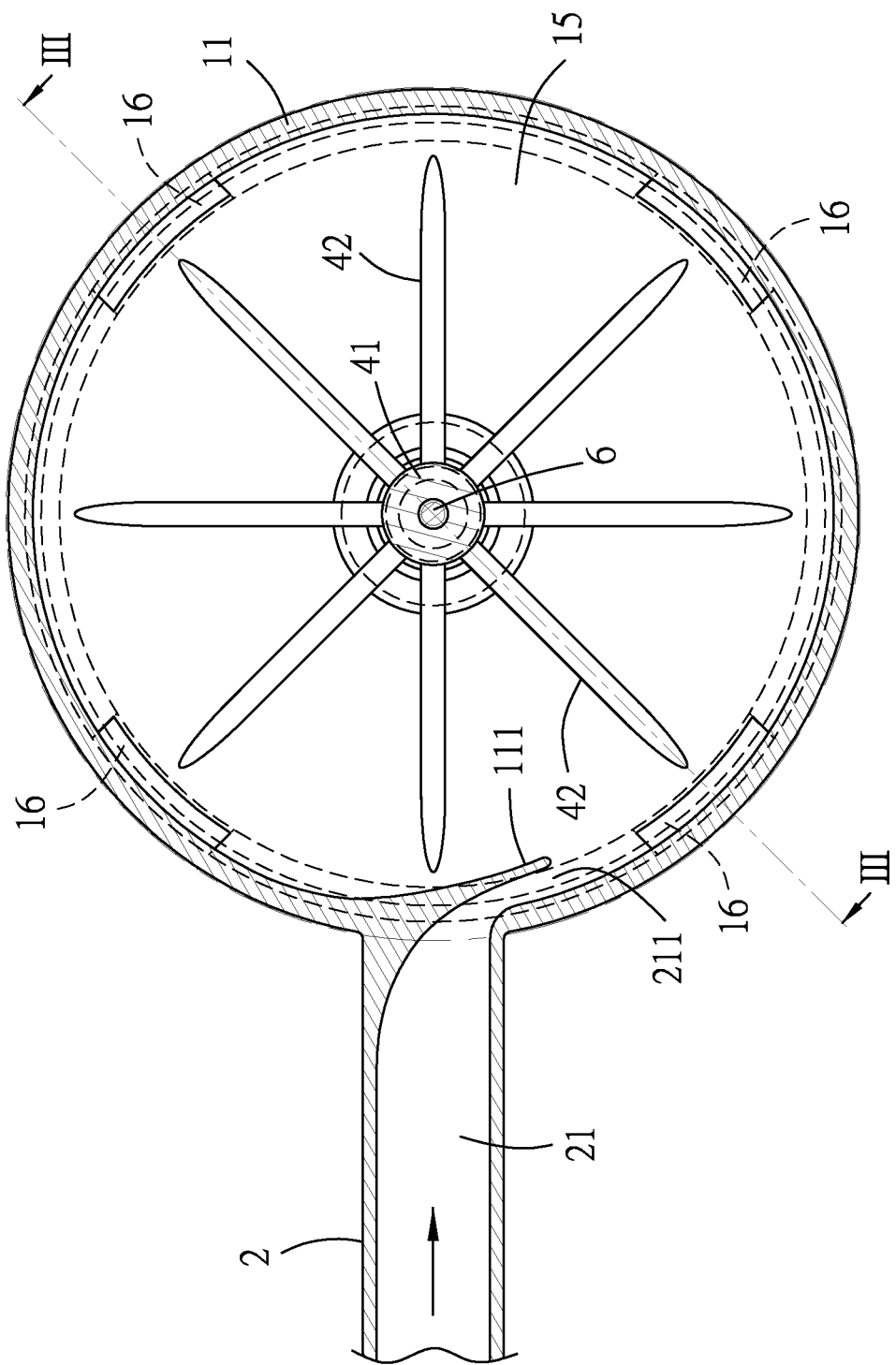
FIG. 2 is a fragmentary sectional view taken along line II-II in FIG. 1.
Figure 3:
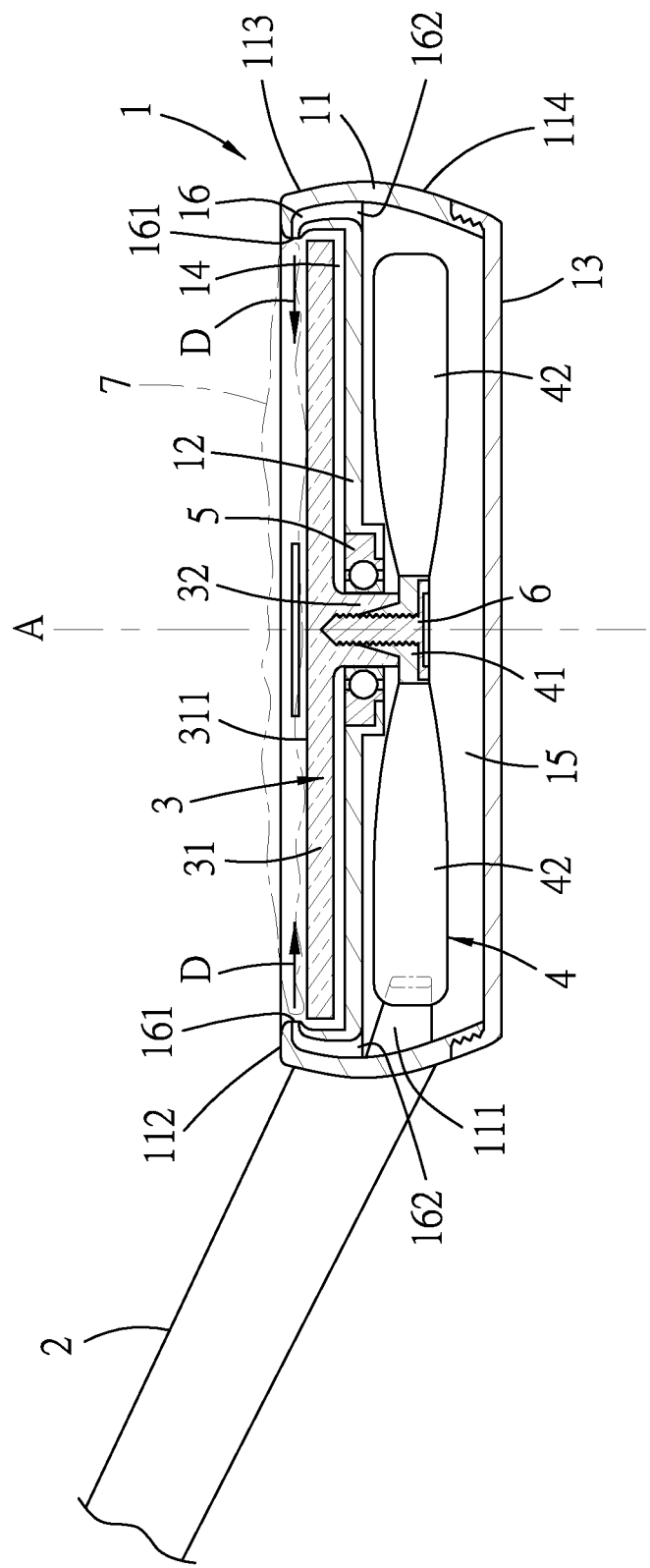
FIG. 3 is a fragmentary sectional view taken along line III-III in FIG. 2, illustrating the first embodiment in use.

Referring to FIGS. 1 to 3, a first embodiment of a mouth mirror apparatus according to the disclosure includes a handheld module 10 and a rotating mirror module 20.

The handheld module 10 includes a carrier seat 1 and a handle grip 2. The carrier seat 1 has a surrounding wall 11, a mounting wall 12 and a base cover 13.

The surrounding wall 11 surrounds an axis (A). The mounting wall 12 extends transversely to the axis (A), and is surrounded by and connected to the surrounding wall 11. The surrounding wall 11 and the mounting wall 12 cooperatively define first and second receiving spaces 14, 15 that are disposed on two sides of the mounting wall 12 which are opposite along the axis (A), and a plurality of air outlet passages 16 that are embedded angularly at intervals in the surrounding wall 11. Each of the air outlet passages 16 has a first passage open end 161 communicating the first receiving space 14 and a second passage open end 162 communicating the second receiving space 15. The first passage open end 161 of each of the air outlet passages 16 is smaller than the second passage open end 162.

Specifically, the surrounding wall 11 has a thick wall section 113 and a thin wall section 114 that are arranged along the axis (A); the thick wall section 113 surrounds the first receiving space 14 and adjoins the mounting wall 12, and the thin wall section 114 surrounds the second receiving space 15 and adjoins the mounting wall 12. The air outlet passages 16 are embedded in the thick wall section 113 of the surrounding wall 11, and the second passage open ends 162 of the air outlet passages 16 are located proximally to the mounting wall 12.

The base cover 13 covers an opening of the second receiving space 15, and is connected to the thin wall section 114 of the surrounding wall 11. It should be noted that, in the present embodiment, the base cover 13 is provided with an internal thread and the thin wall section 114 of the surrounding wall 11 is provided with an external thread, such that the base cover 13 is threadedly and removably connected to the surrounding wall 11.

The handle grip 2 is transversely connected to an outer surface of the surrounding wall 11 of the carrier seat 1, and cooperates with the surrounding wall 11 to define an air inlet passage 21 in spatial communication with the second receiving space 15. The surrounding wall 11 further has a guiding segment 111 that protrudes from an inner surface of the surrounding wall 11 to define an end section 211 of the air inlet passage 21. The end section 211 extends along a direction inclined with a radial direction of the axis (A) (see FIG. 2).

Specifically, referring to FIGS. 1 to 3 and FIG. 5, the handle grip 2 of the handheld module 10 has a tube body 22 that surrounds the air inlet passage 21, and a valve 23 that is mounted to the tube body 22, and that is operable to move between an open position (see FIG. 1) to open the air inlet passage 21, and a closed position (see FIG. 5) to close the air inlet passage 21. In the present embodiment, the valve 23 is a ball valve that is formed with a ball valve passage 231. When the valve 23 is at the open position, the ball valve passage 231 is in communication with the air inlet passage 21; when the valve 23 is at the closed position, the ball valve passage 231 is not in communication with the air inlet passage 21.

The tube body 22 has one end connected to the outer surface of the surrounding wall 11 of the carrier seat 1, and an opposite end adapted to be connected to an air supply device (not shown), such as an air pump, that forces compressed air into the second receiving space 15 via the air inlet passage 21.

Figure 4:
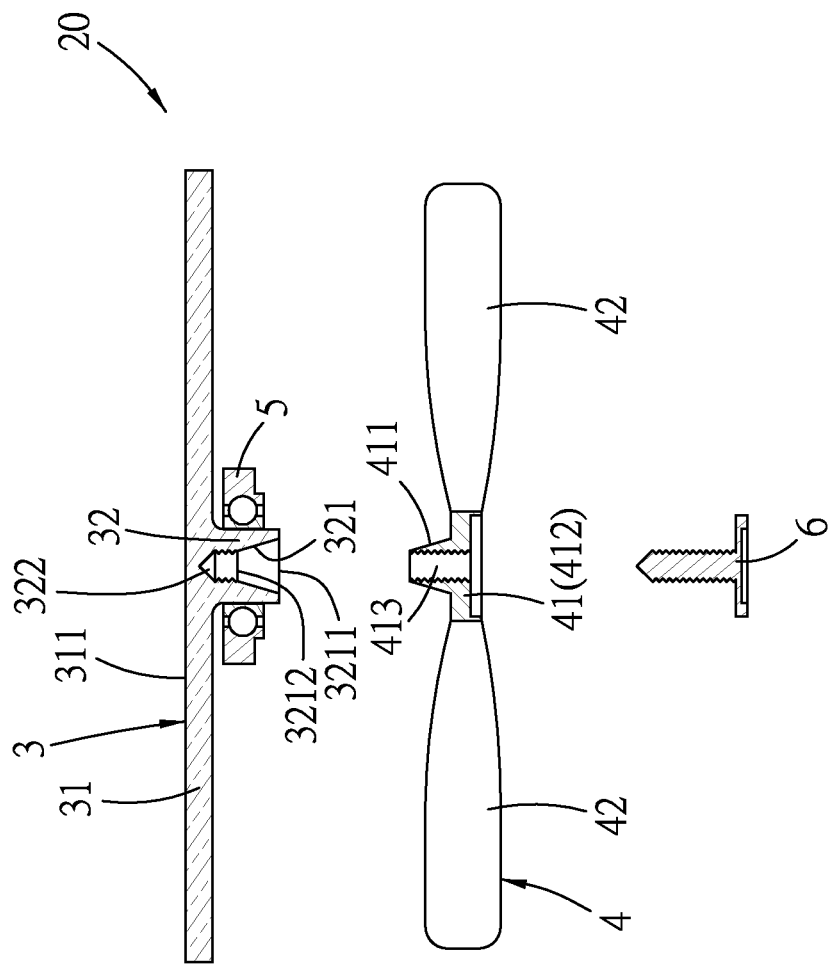
FIG. 4 is an exploded sectional view illustrating a rotating mirror module of the first embodiment.
Figure 5:
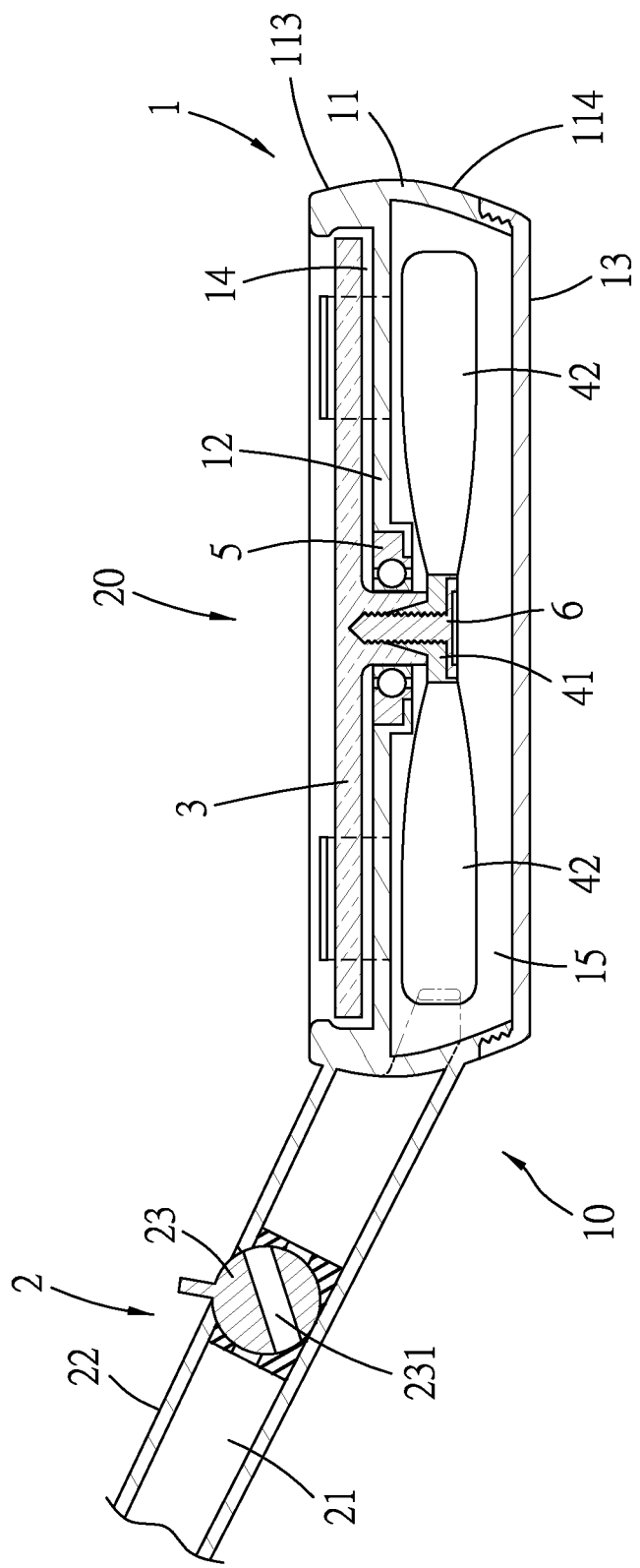
FIG. 5 is a fragmentary sectional view illustrating a valve of the first embodiment at a closed position.

Referring further to FIG. 4, the rotating mirror module 20 includes a mirror unit 3, an impeller 4 and a shaft bearing 5.

The mirror unit 3 has a mirror body 31 and a rotary shaft 32. The mirror body 31 is disposed in the first receiving space 14 of the carrier seat 1 transversely to the axis (A), is rotatable about the axis (A) relative to the carrier seat 1, and has a reflecting surface 311 facing away from the mounting wall 12 of the carrier seat 1. The surrounding wall 11 has a top open end face 112 that is disposed above the reflecting surface 311. The first passage open end 161 of each of the air outlet passages 16 is disposed at a position higher than the reflecting surface 311 and proximal to the top open end face 112, and opens to the first receiving space 14 in an outlet direction (D).

The rotary shaft 32 extends through the mounting wall 12 of the carrier seat 1 along the axis (A), and is co-rotatably connected to the mirror body 31. The shaft bearing 5 is mounted in the mounting wall 12, and is sleeved on the rotary shaft 32.

The impeller 4 has a connecting hub 41, a plurality of fan blades 42 and a screw fastener 6. The connecting hub 41 is disposed in the second receiving space 15, and is co-rotatably connected to the rotary shaft 32. The fan blades 42 are arranged angularly about the axis (A) in the second receiving space 15, are co-rotatably connected to the connecting hub 41, and are adapted to be driven by air, which travels through the air inlet passage 21 into the second receiving space 15, to drive the rotation of the mirror body 31 of the mirror unit 3 relative to the carrier seat 1.

Specifically, in the present embodiment, the connecting hub 41 has an insertion segment 411 that is configured as a truncated cone, a blade connecting part 412 that connects the fan blades 42 and the insertion segment 411, and a hub screw hole 413 that extends through the insertion segment 411 and the blade connecting part 412 along the axis (A). The rotary shaft 32 of the mirror unit 3 is formed with a shaft recess 321 that complementarily receives the insertion segment 411 of the connecting hub 41. More specifically, the shaft recess 321 has an outer open end 3211 for entry of the insertion segment 411, and an inner tapering end 3212; the rotary shaft 32 further has a shaft screw hole 322 that is connected to the inner tapering end 3212 of the shaft recess 321. The screw fastener 6 is threadedly inserted into the hub screw hole 413 of the connecting hub 41 and the shaft screw hole 322 of the rotary shaft 32 to secure the connection between the connecting hub 41 and the rotary shaft 32.

It should be noted that, by virtue of the insertion segment 411 of the connecting hub 41 being configured as a truncated cone and being complementarily received in the shaft recess 321 of the rotary shaft 32, a central axis of the connecting hub 41 is easily aligned with a central axis of the rotary shaft 32 without skew. This can ensure that the plane of the rotation of the mirror body 31 is parallel to the plane of the rotation of the fan blades 42, thereby reducing the risk of rotational imbalance and vibration.

It should also be noted that, by virtue of the end section 211 of the air inlet passage 21 extending along the direction inclined with the radial direction of the axis (A), air entering the second receiving space 15 is able to drive the fan blades 42 with a relatively large torque, thus resulting in efficient rotation of the fan blades 42. In addition, a cross section of each of the fan blades 42 may be varied depending on actual needs; for example, the cross section may be S-shaped in a variation of the embodiment. In this case, the rotation of such S-shaped fan blades 42 changes a direction of the air that exits the end section 211 of the air inlet passage 21 toward the second passage open end 162 of each of the air outlet passages 16 (i.e., a directional change of approximately 90 degrees).

During operation, pressurized air is drawn by the air supply device into the air inlet passage 21, and enters the second receiving space 15 to drive rotation of the impeller 4. Then, to exit the second receiving space 15, the air travels through the air outlet passages 16 and is discharged into the first receiving space 14 via the first passage open ends 161 of the air outlet passages 16.

To control the rotation of the impeller 4 and the mirror unit 3, a user may simply use the valve 23 of the handle grip 2 to control airflow in the air inlet passage 21. However, in other embodiments of the disclosure, the mouth mirror apparatus is not limited to such configuration and the valve 23 may be omitted.

In the present embodiment, the first passage open end 161 of each of the air outlet passage 161 is disposed higher than the reflecting surface 311 of the mirror body 31, and the outlet direction (D) of the first passage open end 161 of each of the air outlet passages 16 is parallel to the reflecting surface 311 of the mirror body 31. That is to say, an angle formed between the outlet direction (D) of the first passage open end 161 of each of the air outlet passages 16 and the reflecting surface 311 is zero. In such a manner, an air curtain 7 is formed over the reflecting surface 311 of the mirror body 31.

It should be noted that, as mentioned above, the first passage open end 161 of each of the air outlet passages 16 is smaller than the second passage open end 162, and in virtue of such configuration, when the air travels through the air outlet passages 16, an efflux velocity of the air at the first passage open end 161 is higher than an influx velocity thereof at the second passage open end 162, which helps in creating strong airflows that form the air curtain 7.

During a dental procedure, since a temperature difference between the mirror body 31 and air of an ambient environment (e.g., warm and humid air in a patient's mouth) can easily cause the reflecting surface 311 of the mirror body 31 to fog up and interrupt the dental procedure, this air curtain 7 is able to isolate the warm and humid air from the reflecting surface 311, thereby preventing the reflecting surface 311 from fogging.

In addition, the air curtain 7 prevents water droplets with debris from hitting the reflecting surface 311 of the mirror body 31, and thus prevents the reflecting surface 311 from damages such as scratches. Furthermore, the air curtain 7 prevents the mirror body 31 from making direct contact with tissues inside the patient's mouth (e.g., gums) during the rotation of the mirror body 31, thereby protecting the tissues.

While the angle formed between the outlet direction (D) of the first passage open end 161 of each of the air outlet passages 16 and the reflecting surface 311 is zero in this embodiment, it may be larger than zero, or not larger than 90 degrees in other embodiments.

Figure 6:
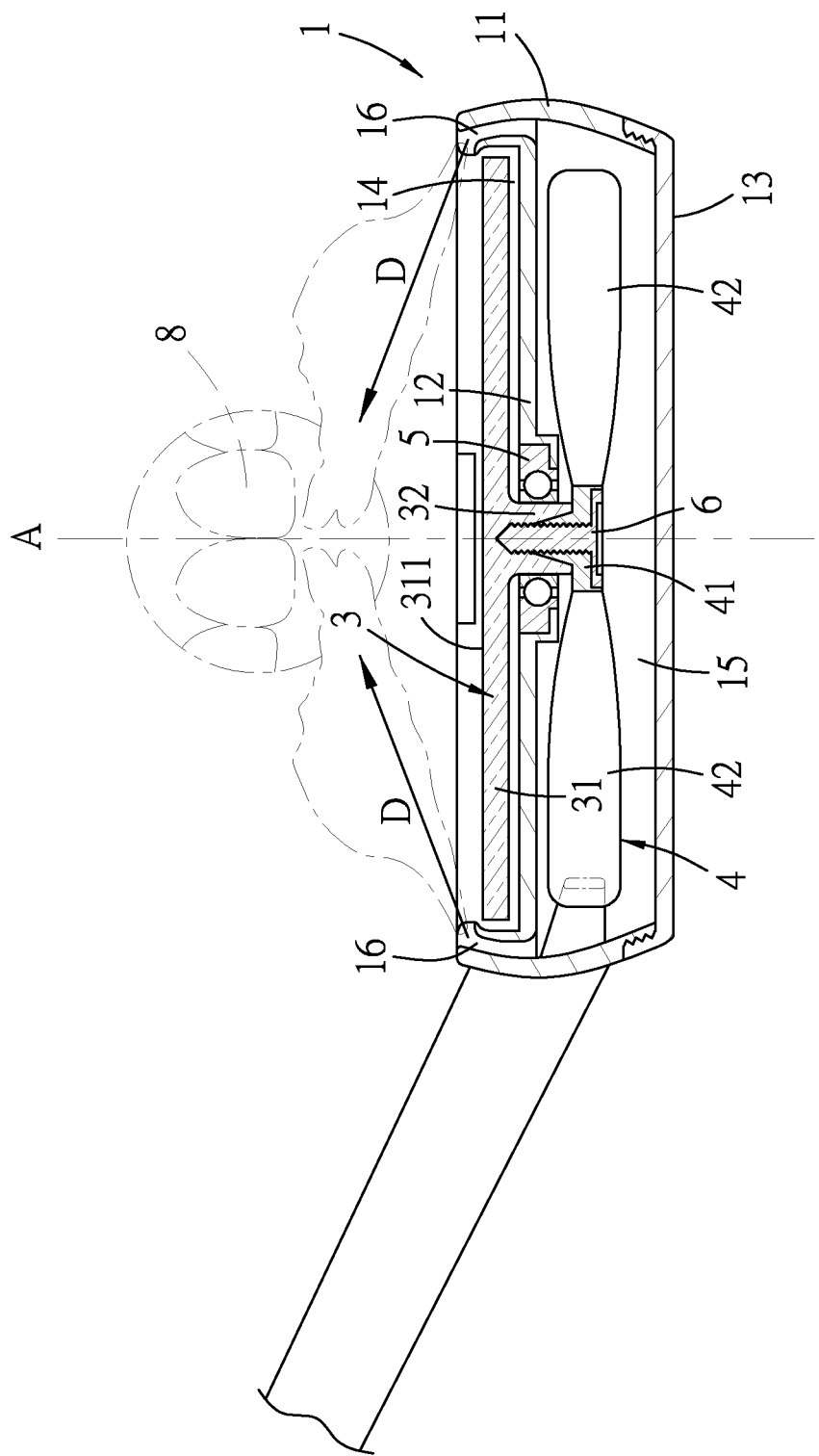
FIG. 6 is a fragmentary sectional view illustrating a second embodiment of the mouth mirror apparatus in use.

Referring to FIG. 6, a second embodiment of the mouth mirror apparatus according to the disclosure is similar to the first embodiment, and the main difference between the two resides in that the angle between the outlet direction (D) of the first passage open end 161 of each of the air outlet passages 16 and the reflecting surface 311 ranges from 30 degrees to 90 degrees.

By virtue of such configuration, when the reflecting surface 311 of the mirror body 31 is disposed close to teeth 8 of the patient, the discharged air can help blow away excessive water splashes or debris on or surrounding the teeth 8, so that the teeth 8 can be properly inspected. Compared with the previous embodiment, such change in orientation of the outlet direction (D) results in different functions to suit different needs.

Moreover, for either one of the embodiments of the disclosure, the angles of the outlet directions (D) of the first passage open ends 161 with respect to the reflecting surface 311 of the mirror body 31 may differ from each other to provide different functions inside the same carrier seat 1.

Figure 7:
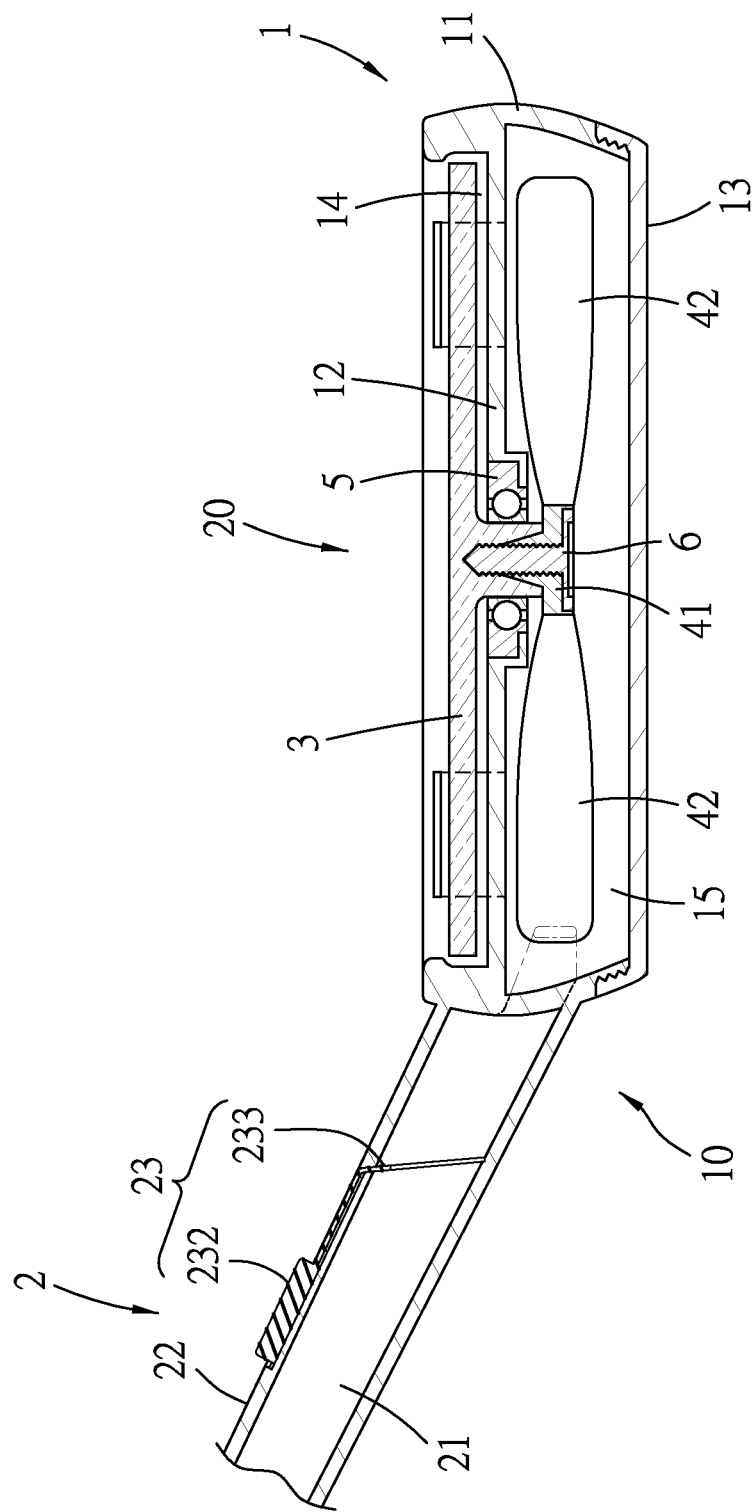
FIG. 7 is a fragmentary sectional view illustrating a third embodiment of the mouth mirror apparatus.
Figure 8:
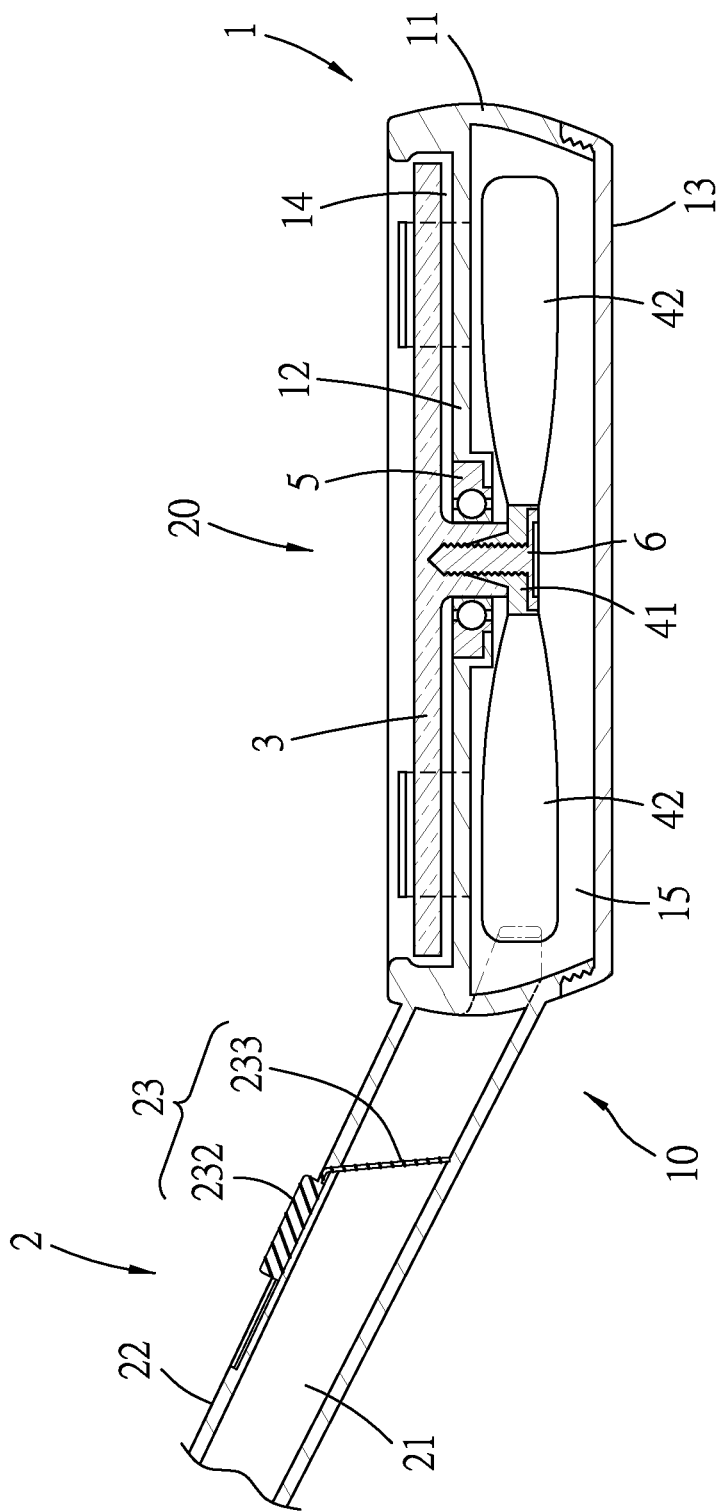
FIG. 8 is a fragmentary sectional view illustrating a valve of the third embodiment at a closed position.

Referring to FIGS. 7 and 8, a third embodiment of the mouth mirror apparatus according to the disclosure is similar to the first embodiment; the main difference between the two is described as follows.

In the present embodiment, the valve 23 of the handle grip 2 has an operating portion 232 that is slidably mounted on the tube body 22, and a blocking portion 233 that is co-movably connected to the operating portion 232.

By pushing or pulling the operating portion 232, the blocking portion 233 is able to close or open the air inlet passage 21 of the tube body 22. Specifically, when the valve 23 is at the open position (see FIG. 7), the blocking portion 233 extends only partially into the tube body 22 so that the air inlet passage 21 is not blocked thereby; when the valve 23 is at the closed position (see FIG. 8), the blocking portion 233 extends completely into the tube body 22 and the air inlet passage 21 is blocked thereby.

Figure 9:
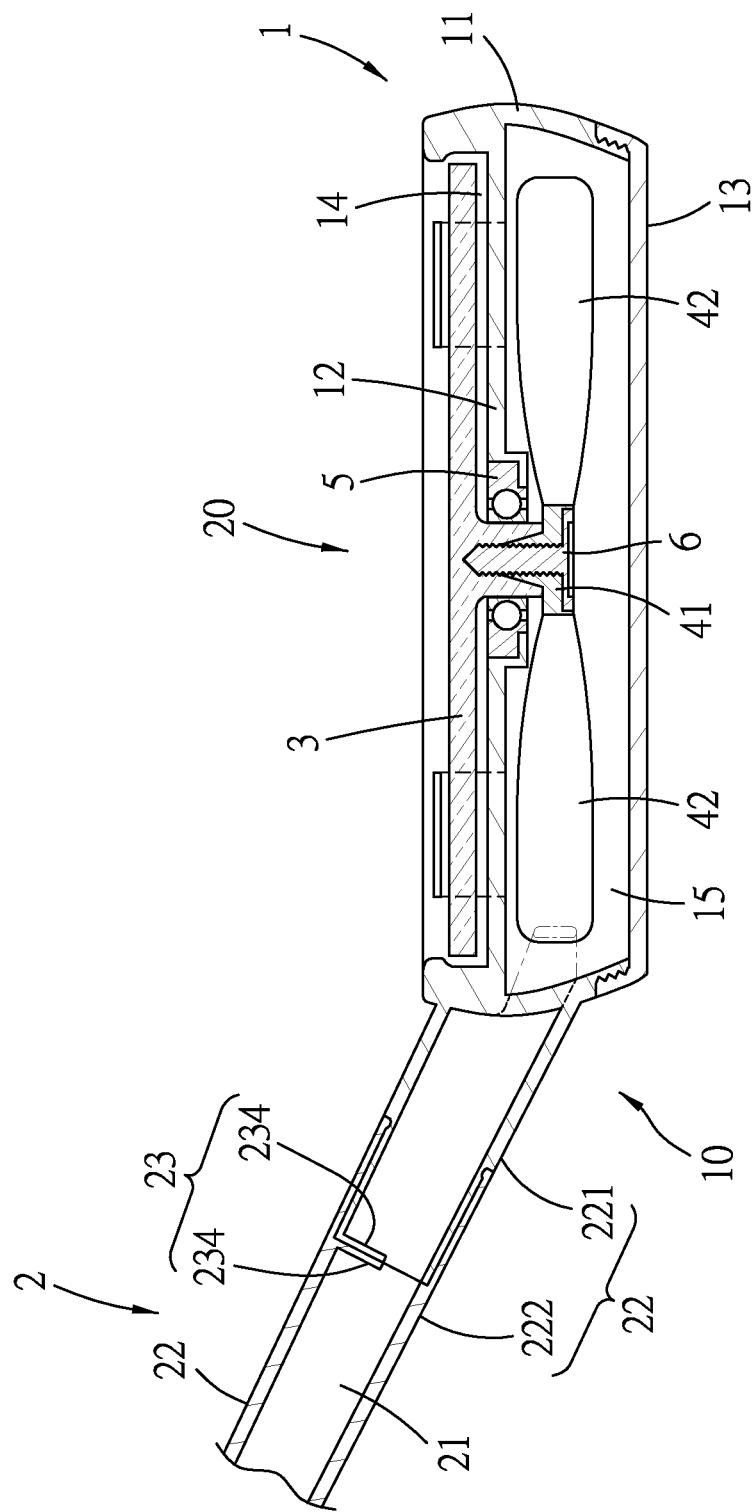
FIG. 9 is a fragmentary sectional view illustrating a fourth embodiment of the mouth mirror apparatus.
Figure 10:
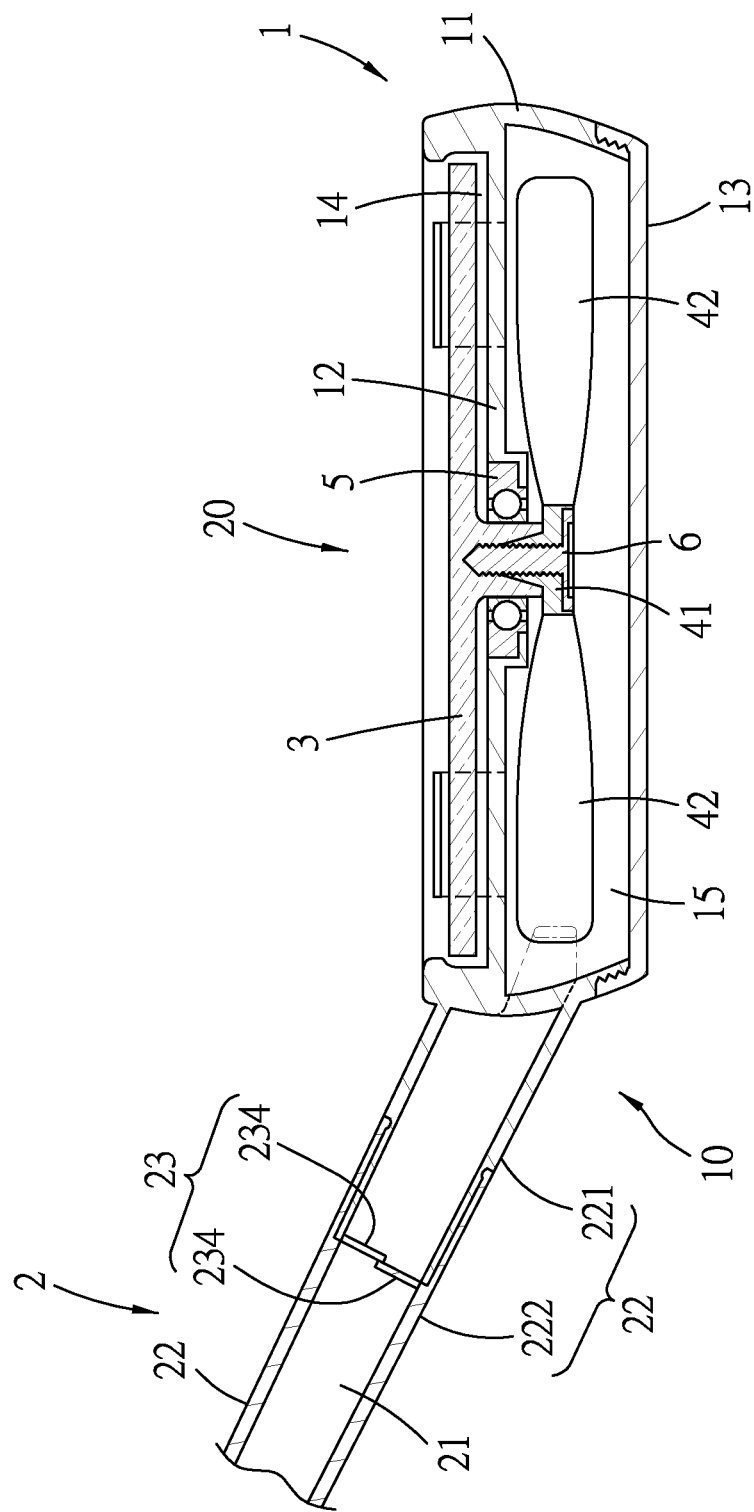
FIG. 10 is fragmentary sectional view illustrating a valve of the fourth embodiment at a closed position.

Referring to FIGS. 9 and 10, a fourth embodiment of the mouth mirror apparatus according to the disclosure is similar to the first embodiment; the main difference between the two is described as follows.

In the present embodiment, the tube body 22 of the handle grip 2 has a stationary segment 221 that is fixedly connected to the carrier seat 1, and a rotating segment 222 that is rotatably sleeved on the stationary segment 221. The valve 23 of the handle grip 2 includes two semicircular stoppers 234 which are respectively connected to the stationary segment 221 and the rotating segment 222. When the valve 23 is at the open position (see FIG. 9), the stoppers 234 overlie each other, so that the air inlet passage 21 is open; when the valve 23 is at the closed position, one of the stoppers 234 is rotated 180 degrees relative to the other one of the stoppers 234, such that the two stoppers 234 form a complete circular barrier that blocks the air inlet passage 21.

In summary, by virtue of the configuration of the rotating mirror module 20 which enables the rotation of the mirror unit 3 as well as the discharge of air via the air outlet passages 16, the air curtain 7 can be formed over the reflecting surface 311 of the mouth mirror apparatus of the present disclosure to prevent the reflecting surface 311 from fogging.

Moreover, by varying configurations of the fan blades 42 (e.g., shape of the cross sections) as well as orientation of the outlet directions (D) of the air outlet passages 16, the mouth mirror apparatus of the present disclosure is able to provide different functions to suit different needs (e.g., preventing water droplets with debris from hitting or attaching to the mirror body 31).

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A mouth mirror apparatus comprising:
a handheld module including
a carrier seat that has
a surrounding wall surrounding an axis,
a mounting wall extending transversely to the axis, and surrounded by and connected to said surrounding wall, said surrounding wall and said mounting wall cooperatively defining
first and second receiving spaces which are disposed on two sides of said mounting wall that are opposite along the axis, and
a plurality of air outlet passages which are embedded angularly at intervals in said surrounding wall, and each of which has a first passage open end communicating with said first receiving space and a second passage open end communicating with said second receiving space, and
a base cover covering an opening of said second receiving space, and being connected to said surrounding wall, and
a handle grip that is transversely connected to an outer surface of said surrounding wall, and that cooperates with said surrounding wall to define an air inlet passage in spatial communication with said second receiving space; and
a rotating mirror module including
a mirror unit that has
a mirror body disposed in said first receiving space transversely to the axis, and being rotatable about the axis relative to the carrier seat, and
a rotary shaft extending through said mounting wall along the axis, and co-rotatably connected to said mirror body, and
an impeller that has
a connecting hub disposed in said second receiving space, and co-rotatably connected to said rotary shaft, and
a plurality of fan blades arranged angularly about the axis in said second receiving space, and co-rotatably connected to said connecting hub, said fan blades being adapted to be driven by air, which travels through said air inlet passage into said second receiving space, to drive the rotation of said mirror body of said mirror unit relative to the carrier seat;
wherein:
said mirror body of said mirror unit has a reflecting surface facing away from said mounting wall of said carrier seat;
said surrounding wall has a top open end face disposed above said reflecting surface;
said first passage open end of each of said air outlet passages is disposed at a position higher than said reflecting surface and proximal to said top open end face, and opens to said first receiving space in an outlet direction; and
an angle is formed between the outlet direction and said reflecting surface and is not larger than 90 degrees.

2. The mouth mirror apparatus as claimed in claim 1, wherein the angle between the outlet direction of said first passage open end of each of said air outlet passages and said reflecting surface is smaller than 90 degrees.

3. The mouth mirror apparatus as claimed in claim 2, wherein the outlet direction of said first passage open end of each of said air outlet passages is parallel to said reflecting surface.

4. The mouth mirror apparatus as claimed in claim 2, wherein the angle between the outlet direction of said first passage open end of each of said air outlet passages and said reflecting surface ranges from 30 degrees to 90 degrees.

5. The mouth mirror apparatus as claimed in claim 1, wherein said surrounding wall of said carrier seat of said handheld module has a guiding segment that protrudes from an inner surface of said surrounding wall to define an end section of said air inlet passage, said end section extending along a direction inclined with a radial direction of the axis.

6. The mouth mirror apparatus as claimed in claim 1, wherein said handle grip of said handheld module has:
a tube body that surrounds said air inlet passage; and
a valve that is mounted to said tube body, and that is operable to move between an open position to open said air inlet passage, and a closed position to close said air inlet passage.

7. A mouth mirror apparatus comprising:
a handheld module including
a carrier seat that has
a surrounding wall surrounding an axis,
a mounting wall extending transversely to the axis, and surrounded by and connected to said surrounding wall, said surrounding wall and said mounting wall cooperatively defining
first and second receiving spaces which are disposed on two sides of said mounting wall that are opposite along the axis, and
a plurality of air outlet passages which are embedded angularly at intervals in said surrounding wall, and each of which has a first passage open end communicating with said first receiving space and a second passage open end communicating with said second receiving space, and
a base cover covering an opening of said second receiving space, and being connected to said surrounding wall, and
a handle grip that is transversely connected to an outer surface of said surrounding wall, and that cooperates with said surrounding wall to define an air inlet passage in spatial communication with said second receiving space; and
a rotating mirror module including
a mirror unit that has
a mirror body disposed in said first receiving space transversely to the axis, and being rotatable about the axis relative to the carrier seat, and
a rotary shaft extending through said mounting wall along the axis, and co-rotatably connected to said mirror body, and
an impeller that has
a connecting hub disposed in said second receiving space, and co-rotatably connected to said rotary shaft, and
a plurality of fan blades arranged angularly about the axis in said second receiving space, and co-rotatably connected to said connecting hub, said fan blades being adapted to be driven by air, which travels through said air inlet passage into said second receiving space, to drive rotation of said mirror body of said mirror unit relative to the carrier seat;

wherein:
said connecting hub of said impeller has an insertion segment that is configured as a truncated cone; and
said rotary shaft of said mirror unit is formed with a shaft recess that complementarily receives said insertion segment of said connecting hub of said impeller.

8. The mouth mirror apparatus as claimed in claim 7, wherein:
said connecting hub further has a blade connecting part connecting said fan blades and said insertion segment, and a hub screw hole extending through said insertion segment and said blade connecting part;
said shaft recess has an outer open end for entry of said insertion segment, and an inner tapering end;
said rotary shaft further has a shaft screw hole connected to said inner tapering end of said shaft recess; and
said impeller further has a screw fastener threadedly inserted into said hub screw hole and said shaft screw hole.

9. The mouth mirror apparatus as claimed in claim 7, wherein an angle between an outlet direction of said first passage open end of each of said air outlet passages and said reflecting surface is smaller than 90 degrees.

10. The mouth mirror apparatus as claimed in claim 9, wherein the outlet direction of said first passage open end of each of said air outlet passages is parallel to said reflecting surface.

11. The mouth mirror apparatus as claimed in claim 9, wherein the angle between the outlet direction of said first passage open end of each of said air outlet passages and said reflecting surface ranges from 30 degrees to 90 degrees.

12. The mouth mirror apparatus as claimed in claim 7, wherein said surrounding wall of said carrier seat of said handheld module has a guiding segment that protrudes from an inner surface of said surrounding wall to define an end section of said air inlet passage, said end section extending along a direction inclined with a radial direction of the axis.

13. The mouth mirror apparatus as claimed in claim 7, wherein said handle grip of said handheld module has:
a tube body that surrounds said air inlet passage; and
a valve that is mounted to said tube body, and that is operable to move between an open position to open said air inlet passage, and a closed position to close said air inlet passage.

\* \* \* \* \*